United States Patent [19]

Shih

[11] Patent Number: 5,617,213

[45] Date of Patent: Apr. 1, 1997

[54] SPOT MICRODENSITOMETER FOR SPECTRAL DENSITY ANALYSIS OF FILM

[76] Inventor: Sun-Fu Shih, 2208 NW. 29th St., Gainesville, Fla. 32605

[21] Appl. No.: 408,207

[22] Filed: Mar. 22, 1995

[51] Int. Cl.$^6$ .................................................. G01N 21/00
[52] U.S. Cl. ............................................ 356/443; 356/444
[58] Field of Search .................................. 356/443–444; 250/559.02

[56] References Cited

U.S. PATENT DOCUMENTS

| | | | |
|---|---|---|---|
| 2,649,834 | 8/1953 | Sweet | 356/443 |
| 3,525,571 | 8/1970 | Gebel | 356/444 |
| 3,741,664 | 6/1973 | Torin | 250/559.02 |
| 3,856,417 | 12/1974 | Bey et al. | 356/443 |
| 3,942,898 | 3/1976 | Anderson | 356/443 |
| 3,994,587 | 11/1976 | Yamamoto et al. | 356/444 |
| 3,994,593 | 11/1976 | Kato et al. | 356/444 |
| 4,150,899 | 4/1979 | Nakamura | 356/444 |
| 4,229,107 | 10/1980 | Childers | 356/443 |
| 4,229,108 | 10/1980 | Childers | 356/443 |
| 4,329,591 | 5/1982 | Fujiwara et al. | 356/444 |
| 4,338,033 | 7/1982 | Kato | 356/444 |
| 4,533,253 | 8/1985 | Okano | 356/443 |
| 4,551,023 | 11/1985 | Nakauchi | 356/444 |
| 4,946,282 | 8/1990 | Task | 356/443 |

Primary Examiner—Frank G. Font
Assistant Examiner—Jason D. Vierra Eisenberg
Attorney, Agent, or Firm—Paul S. Rooy

[57] ABSTRACT

A spot densitometer system comprising a viewing assembly, a photodetection apparatus optically connected to the viewing assembly, and a computer interface electrically connected to the photodetection apparatus. The viewing assembly comprises a flat spectrum lamp, condensing lens, film handler, focusing lens comprises a photomultiplier tube optically connected to the viewing assembly, a monochromator electrically connected to the photomultiplier tube, and a control unit electrically attached to the photomultiplier tube and the monochromator. The computer interface comprises an analog to digital card and signal processing software, which convert analog electrical signals from the photodetection apparatus into useful output formats such as color density, relative exposure, and log relative exposure. The position of the film emulsion whose density is being measured may be adjusted vertically and horizontally.

12 Claims, 4 Drawing Sheets

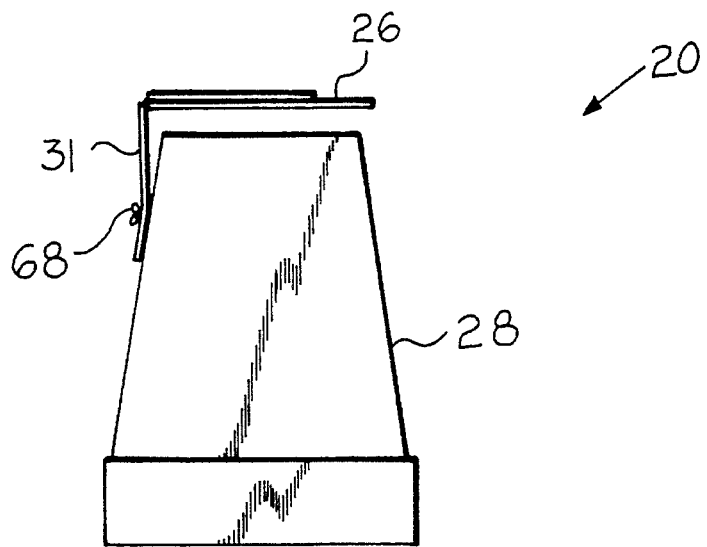
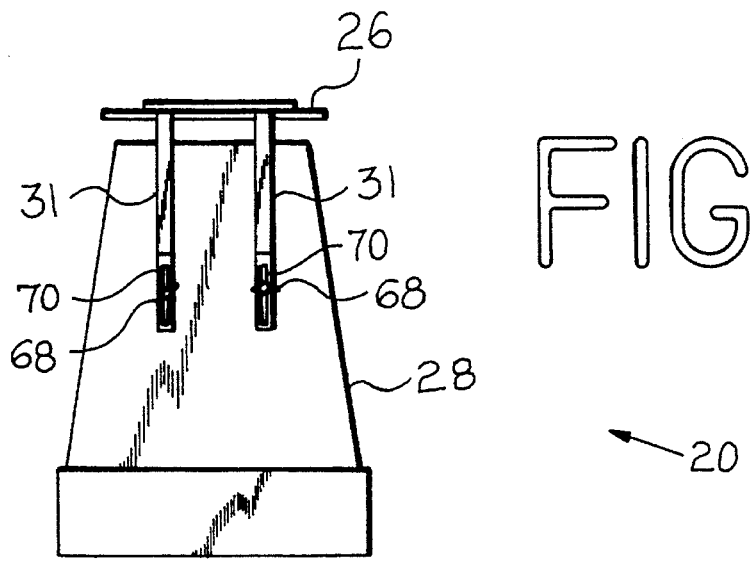

SPOT MICRODENSITOMETER FOR SPECTRAL DENSITY ANALYSIS OF FILM

BACKGROUND OF THE INVENTION

FIELD OF THE INVENTION

This invention relates to densitometers, and in particular to a spot microdensitometer system.

BACKGROUND OF THE INVENTION

One way to measure exposure density of photographic film emulsions is to employ a densitometer for the purpose. When a small area of film is to be measured, a spot densitometer is used.

Spot densitometers are especially useful when measuring the exposure density of film emulsions used in satellite photography, such as aerial color infrared film diaspositives. Satellites used for this type of photography include Landsat, SPOT, IRS, J-ERS-1, EOS and Landsat 7. Microdensitometrically processed aerial color infrared film data may be used for a wide variety of remote sensing projects: environment studies, artesian well identification, vegetation indexing, ground-truth for satellite land-cover studies, crop health, crop nutrient content, crop water stress, monitoring forest health and hydrologic conditions, etc.

Spot microdensitometry is essential to the calibration of aerial color infrared film relative exposure values, and the correction of aerial color infrared film relative exposure values for geometric effects (exposure fall-off). Spot microdensitometry is also useful in providing aerial color infrared film-based reflectance data for the calibration of images from aerial scanners and satellites.

Currently existent spot microdensitometers generally incorporate a number of components. A light source shines through the film whose density is to be measured. An aperture assembly defines the size of the area of film emulsion to be measured for density. A filter assembly permits the interposition of filters to select the spectral bands over which the density will be measured. Light source light which has passed through the aperture, filter, and film emulsion is collected by a photoelectric receiver such as a photomultiplier tube, which converts the light energy into electrical energy output. This electrical output is converted logarithmically by suitable electronics into digitally represented density values, which may be displayed on an oscilloscope or recorded on computer compatible tape.

There are a number of problems associated with current spot densitometer designs. The light from the light source may include infrared light, which may burn the film emulsion whose density is being measured.

In Addition, current designs may suffer from the disadvantage of difficult sample size adjustment. Also, it may be difficult to accurately position the film emulsion sample to be measured on a horizontal plain. Finally, current designs lack a film advance mechanism.

SUMMARY OF THE INVENTION

Accordingly, it is an object of the present invention to provide a spot microdensitometer system which prevents infrared light from impinging on a film emulsion whose density is being measured. Design features allowing this object to be accomplished include a flat spectrum lamp and a condensing lens. An advantage associated with the accomplishment of this object in the prevention of film emulsion burning.

It is another object of the present invention to provide a spot microdensitometer system whose film sample size is easily controlled. Design features allowing this object to be accomplished include a lower plate and means of adjusting the vertical position of the lower plate. Benefits associated with the accomplishment of this object include increased case of use and consequent increased use efficiency.

It is another object of this invention to provide a spot microdensitometer system which allows fast and easy horizontal plain positioning of the film emulsion whose density is to be measured. Design features enabling the accomplishment of this object include a means of adjusting the horizontal position of the film emulsion over the plain of the lower plate. Advantages associated with the realization of this object include faster and more efficient density measuring and consequent cost savings.

It is still another object of this invention to provide a spot microdensitometer which accommodates roles of film. Design features allowing this object to be achieved include film spool carriers and film axle cranks. Benefits associated with reaching this objective include the faster and easier use associated with the capability of handling rolls of film, and consequent cost savings.

BRIEF DESCRIPTION OF THE DRAWINGS

The invention, together with the other objects, features, aspects and advantages thereof will be more clearly understood from the following in conjunction with the accompanying drawings.

Four sheets of drawings are provided. Sheet one contains FIG. 1. Sheet two contains FIGS. 2 and 3. Sheet three contains FIGS. 4 and 5. Sheet four contains FIGS. 6 and 7.

FIG. 6 is a side view of a viewing assembly with lower plate vertical adjustment capability.

FIG. 7 is a rear view of a viewing assembly with lower plate vertical adjustment capability.

DETAILED DESCRIPTION OF THE PREFERRED EMBODIMENT

Figure 1:
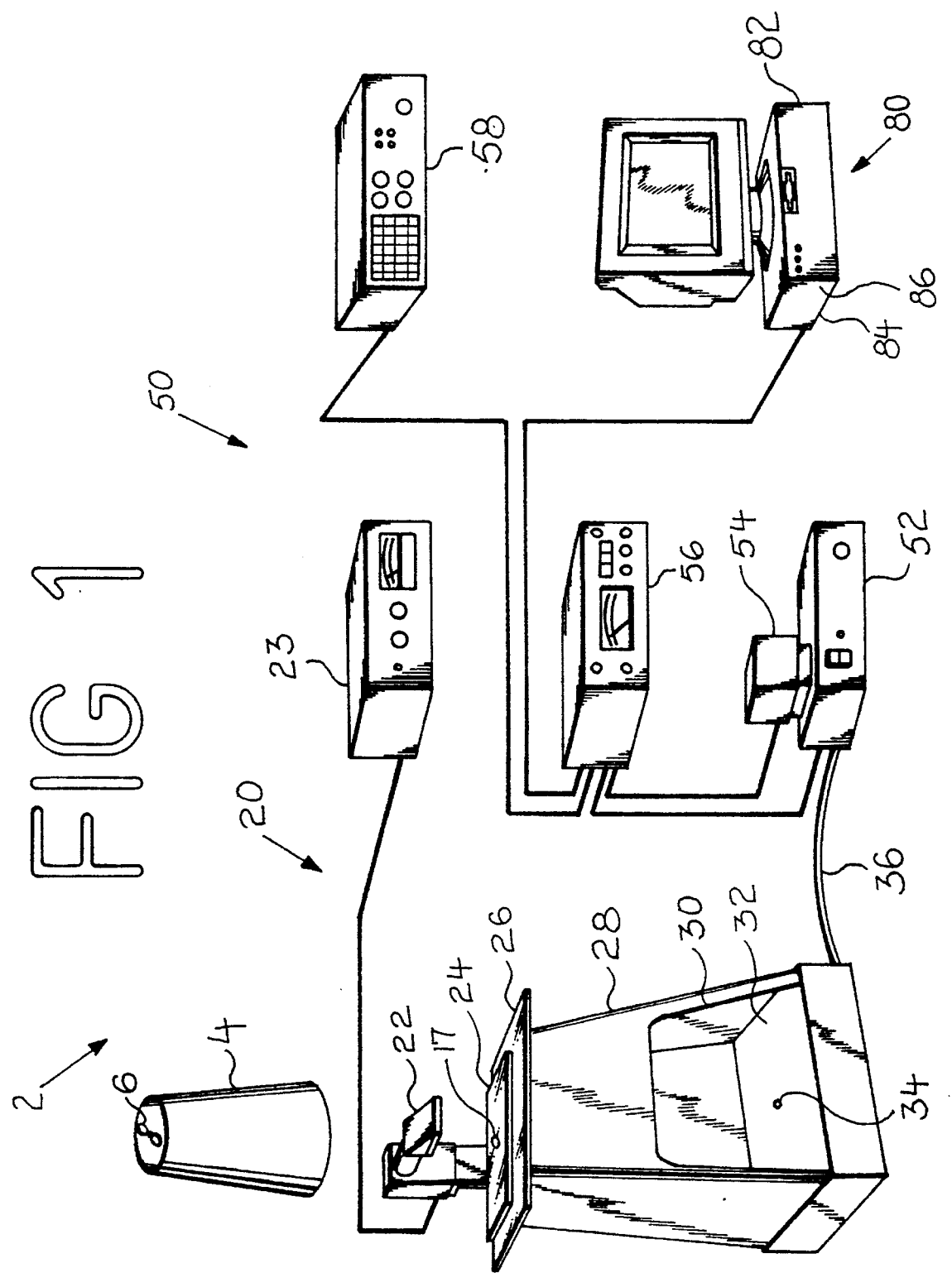
FIG. 1 is a schematic view of a spot microdensitometer system.

FIG. 1 is a schematic view of spot microdensitomer system 2. Spot microdensitometer system 2 is comprised of viewing assembly 20, photodetection apparatus 50, and computer interface 80.

Figure 4:
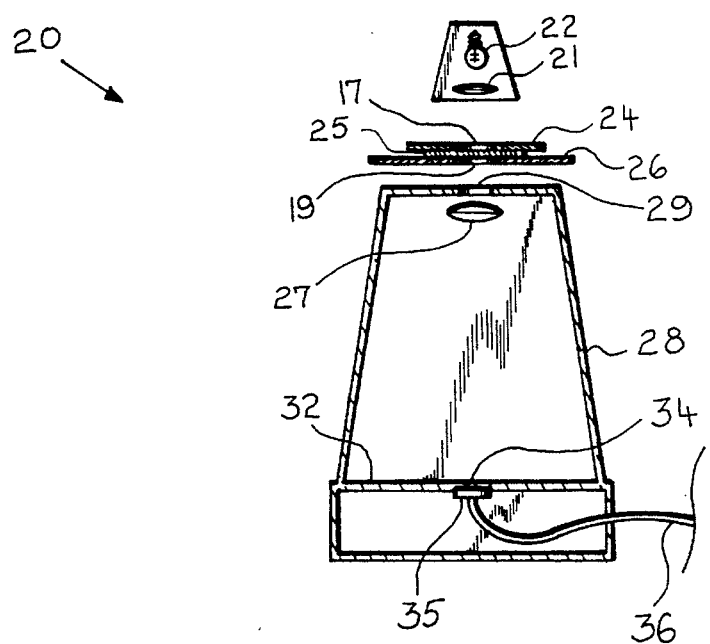
FIG. 4 is a front cross-sectional schematic view of a viewing assembly.

Referring also to FIG. 4, viewing apparatus 20 comprises flat spectrum lamp 22 which projects light through condensing lens 21, upper plate aperture 17, film 25, lower plate aperture 19, housing top aperture 29, focusing lens 27, and viewing spot 34, onto optic cable receptor 35. Electrical power for flat spectrum lamp 22 is supplied by power supply 23. Ambient air surrounding flat spectrum lamp 22 is pulled through exhaust chimney 4 by exhaust fan 6. This exhaust function serves to cool flat spectrum lamp 22 and to remove ozone produced by its operation.

Flat spectrum lamp 22, condensing lens 21, upper plate 24, film 25, lower plate 26 and focusing lens 27 are supported by housing 28. Housing 28 comprises housing front aperture 30 through which housing floor 32 is visible. Housing floor 32 comprises viewing spot 34, through which light from flat spectrum lamp 22 passes en route to optic fiber cable receptor 35.

Figure 2:
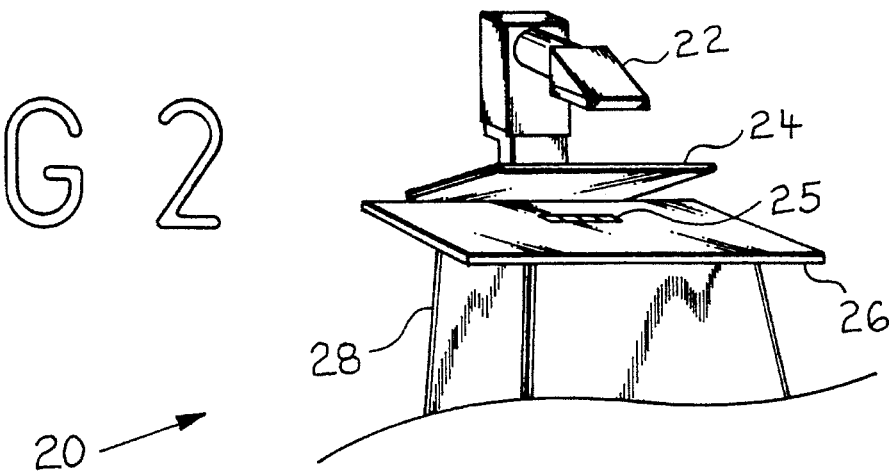
FIG. 2 is a front quarter isometric view of a viewing assembly.

As may be observed in FIG. 2, upper plate 24 is rotatably attached to lower plate 26. When upper plate 24 is rotated away from lower plate 26 as is depicted in FIG. 2, film 25 may be positioned on lower plate 26, and then upper plate 24 lowered, thereby trapping film 25 into position between upper plate 24 and lower plate 26.

Figure 3:
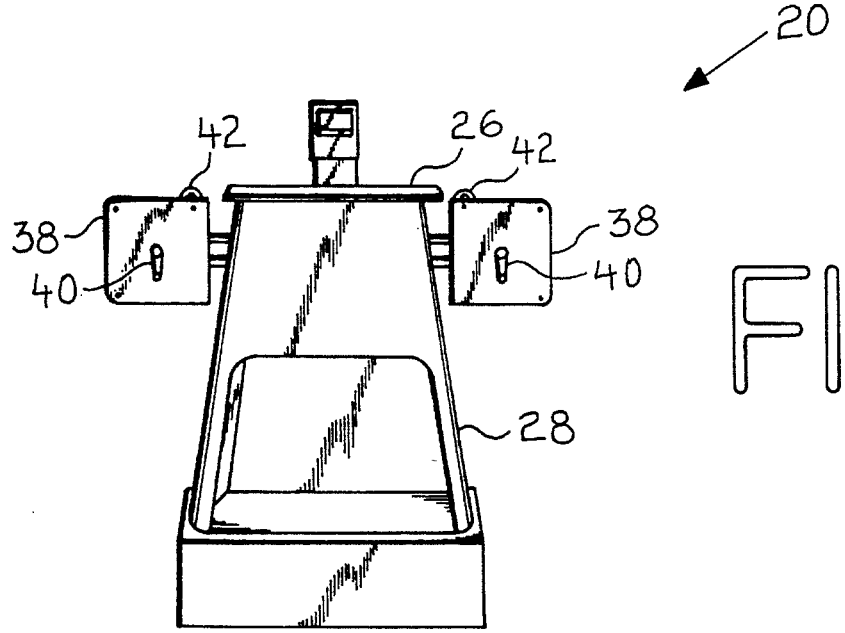
FIG. 3 is a front view of a viewing assembly with film roll handling capability.
Figure 5:
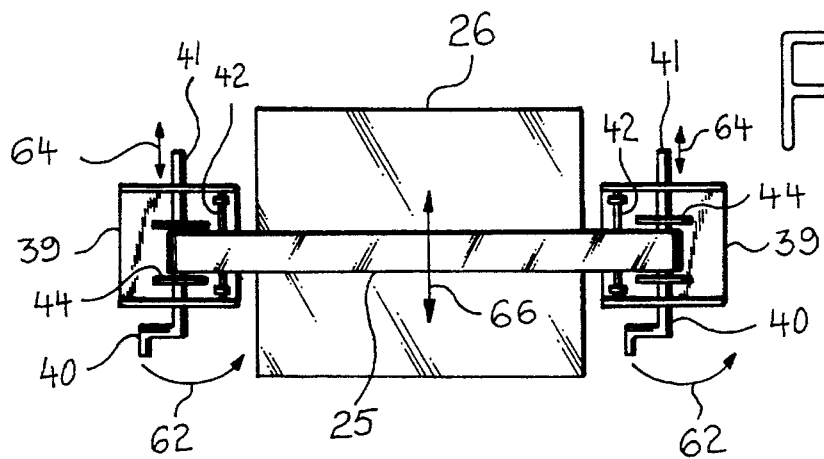
FIG. 5 is a top view of a lower plate with film roll handling capability.

Viewing assembly 20 may also incorporate film handling capability as illustrated in FIGS. 3 and 5. Film spool carriers 38 are attached to housing 28. Each film spool carrier 38 comprises carrier housing 39, roller 42, film spool 44, film spool axle 41, and film axle crank 40. Film spool axle 41 is rotatably and slidably attached to carrier housing 39. Film spool 44 is mounted to film spool axle 41, and film axle crank 40 is rigidly attached to film spool axle 41. Film 25 is wound around film spools 44, so that turning film axle cranks 40 as indicated by rotation arrows 62 advances film 25 over lower plate 26 as desired into an optimum position to measure the density of the film exposure.

Axles 41 are slidably attached to carrier housings 39 so that they may translate axially relative to carrier housings 39 and lower plate 26 as indicated by arrows 64. The act of translating spool axles 41 as indicated by arrows 64 also translates film spools 44 axially, and moves film 25 across lower plate 26 as indicated by arrow 66 as desired into an optimum position to measure the density of the film exposure.

The optical height of film 25 relative to optic cable receptor 35 may be adjusted in two ways. First, the focus of focusing lens 27 may be changed. Second, as illustrated in FIGS. 6 and 7, lower plate 26 is slidably attached to housing 28 by means of lower plate supports 31. Each lower plate support 31 comprises a lower plate support slot 70. Lower plate supports 31 are attached to housing 28 by means of butterfly bolts 68 sized to fit through lower plate support slots 70. The height of lower plate 26 may be adjusted by loosening butterfly bolts 68, sliding lower plate 26 to the desired height, and then tightening butterfly bolts 68, thereby securely locking lower plate 26 into the desired height.

After passing through condensing lens 21, upper plate aperture 17, film 25, lower plate aperture 19, housing top aperture 29, focusing lens 27, and viewing spot 34, light from flat spectrum lamp 22 impinges on optic cable receptor 35. Fiber optic cable 36 optically connects optic cable receptor 35 and photomultiplier tube 52. The input of control unit 56 is electrically connected to photomultiplier tube 52 and monochrometer 54. The output of control unit 56 is electrically connected to oscilloscope 58 and computer 82.

Computer interface 80 comprises digital computer 82 electrically connected to the output of control unit 56. Computer 82 contains analog to digital card 84, and signal processing software 86.

In the preferred embodiment, flat spectrum lamp 22 was an Oriel model 6251 75 w Xenon, and power supply 23 was an Oriel model 6301. Condensing lens 21 was an Oriel model 6327 Pyrex; focusing lens 27 was an Oriel model 6198. Monochromator 54 was a Rofin-Sinar model RSO 6000, and photomultiplier tube 52 was a Rofin-Sinar model 6117. Control unit 56 was a Monolight model 6200.

Housing 28 maybe fabricated of metal, plastic, or other appropriate material. Upper plate 24 and lower plate 26 may be fabricated of transparent plastic, glass, Plexiglas, or other appropriate material.

Operation

In operation, power supply 23 provides electrical power to flat spectrum lamp 22. Exhaust chimney 4 and exhaust fan 6 serve for cooling and ozone removal. In the preferred embodiment, power supply 23 was a regulated power supply which achieved low (0.2% nms maximum) light ripple. Light passes through condensing lens 21, which removes infrared light that could cause excessive heating and possible burning, of film 25. Filters such as gelatin filters may also be interposed between flat spectrum lamp 22 and film 25 in order to isolate trace portions as desired.

Film 25 is trapped between transparent upper plate 24 and transparent lower plate 26, which hold film 25 in position. Light from flat spectrum lamp 22 passes through condensing lens 21, upper plate aperture 17, film 25, lower plate aperture 19, housing top aperture 29 and focusing lens 27, and on through viewing spot 34, to impinge on optic cable receptor 35. Focusing lens 27 is adjustable to focus the film 25 image on optic cable receptor 35.

Fiber optic cable 36 has its optic cable receptor 35 end attached beneath viewing spot 34 in housing floor 32. Optical signals are converted into analog electrical signals by photomultiplier tube 52, monochromator 54 and control unit 56. The output of control unit 56 is connected to oscilloscope 58 and computer 82. Oscilloscope 58 displays the trace at the same time that the trace is sampled by computer signal processing software 86, so that the user can be sure that the spot densitometer system 2 is operating properly. Control unit 56 provides a cursor for the oscilloscope trace, records traces with a controlled time increment, and allows transmission of traces to the computer interface.

Computer interface 80 comprises analog to digital card 84 and signal processing software 86. The data in the traces consist of time (ms) and voltage (mv) values. The time values must be calibrated to wavelength values; this is done by a linear calibration of trace time to wavelength at identifiable points. Point for calibration should include the trace trigger-setting as the short-wavelength point, plus a laser pulse (about 600 nm) as a high-wavelength point. The resulting conversion equation is of the form:

$$W=A*T+B$$

Where W=wavelength (nm), T=trace time (ms), and A and B are constants. The wavelength increment of the traces should be about 1–2 nm.

Example of Application

Aerial color infrared (ACIR) film produces a false-color record by representing original scene reflectances in the wavelengths of green, red and near-infrared in varying densities of emulsion colors of blue, green, and red, respectively (see J. F. Fleming, STANDARDIZATION TECHNIQUES FOR AERIAL COLOUR INFRARED FILM (Interdepartmental Committee on Air Surveys (ICAS) Technical Publication, Stock No. SMP-1253B, Ottawa, Canada, 1980). Therefore, three gelatin filters (Kodak Wratten 25, 58 and 47B) may be used to isolate the portions of the trace corresponding to the blue, green, and red emulsion peaks of Kodak 2443 ACIR film. Each emulsion peak corresponds to five trace time increments, so that five voltage values are averaged to produce a single output voltage value for each emulsion false-color. The trace times and wavelengths which correspond to each false color are given in Table 1:

TABLE 1

APPLICATION EXAMPLE EMULSION PEAK VALUES

| False Color Emulsion Peak | Trace Time(s) | Wavelength (nm) |
|---|---|---|
| Blue | 0.00287 | 436.1 |
| | 0.00288 | 437.5 |
| | 0.00289 | 438.9 |
| | 0.00290 | 440.3 |
| | 0.00292 | 443.2 |
| Green | 0.00347 | 521.1 |
| | 0.00348 | 522.5 |
| | 0.00349 | 523.9 |
| | 0.00350 | 525.3 |
| | 0.00352 | 528.2 |
| Red | 0.00413 | 614.6 |
| | 0.00414 | 616.0 |
| | 0.00415 | 617.4 |
| | 0.00416 | 618.8 |
| | 0.00418 | 621.7 |

A program is employed to clip the large trace files and convert them into short files containing only density values for the three false-colors. Density calculation requires two trace files—one of the filmed spot of interest, and one of the light source alone. Density calculation is performed according to the equation (see T. M. LILLESAND & R. W. KIEFER, REMOTE SENSING AND IMAGE INTERPRETATION(John Wiley & Sons, N.Y., 1979):

$$D_c = \log(S_c/F_c)$$

where $D_c$=density (unitless) for false-color c, $S_c$=light-source trace value (mv) for false-color c, and $F_c$=film trace value (mv) far false-color c.

Density values alone do not give an accurate spectral signature of a filmed object, due to geometric fall-of effects and the nonlinear relation of ACIR film exposure to object reflectances (see LILLESAND & KIEFER; FLEMING). In order to obtain spectral signatures from a roll of ACIR film diapositives, densitometric measurement must first be performed on the roll's step wedge (see, J. D. Jordan, Application of Remote Sensing Techniques to Abandoned Well Assessment in Lee County, Fla. (1987) (unpublished Masters thesis, University of Florida); LILLESAND & KIEFER). From the known relative log-exposure (RLE) values and measured densities of the wedges, curves of density vs. RLE (D-logE curves) can be plotted for blue, green, and red false-colors. Then any subsequent set of density measurements can be converted into RLE values. This conversion can be done by hand or by a program which mathematically models the D-logE curves. Note that each roll of ACIR film well have its own unique set of D-logE curves (also influenced by the particular densitometer used). The importance of RLE values is due to the fact that relative-exposure (RE) values, obtained by taking the analog of RLE values, can be corrected for fall-off effects by normalization, and that these normalized RE values (and not densities) more accurately represent the reflective reflectances of the original object (LILLESAND & KIEFER).

Normalization of RE values to eliminate fall-off effects requires knowledge of both the radial distance (r) from the photograph center to the object of interest, and the camera constants for the particular camera used in the ACIR mission. Since the camera constants (for blue, green and red) are seldom provided by the photographers, they must be calculated from RE datasets corresponding to pairs of photographs on which the same object is present (Jordan).

Once the camera constants are known, a normalization program can be applied to the RE data. Normalization is performed for each false-color according to the equation (LILLESAND & KIEFER):

$$RE_0 = RE/(\cos \theta)^a$$

$$\theta = \arctan(r/f)$$

where RE=RE at angle θ from the perpendicular $RE_0$=RE that would have resulted if the angle had been zero, r is defined as above, f is the focal length of the camera lens (usually 6 inches), and n is the camera constant. The effect of geometric fall-off is quite serious—without normalization, only RE values taken from a 1-inch diameter circle in the center of a 1:24000 scale ACIR photo will be accurate enough for special signature distinction. In this manner the density of film emulsions may be converted into useful output formats such as color density, relative exposure, and log relative exposure.

While a preferred embodiment of the invention has been illustrated herein, it is to be understood that changes and variations may be made by those skilled in the art without departing from the spirit of the appending claims.

DRAWING ITEM INDEX 2 spot microdensitometer system
4 exhaust chimney
6 exhaust fan
17 upper plate aperture
19 lower plate aperture
20 viewing assembly
21 condensing lens
22 flat spectrum lamp
23 power supply
24 upper plate
25 film
26 lower plate
27 focusing lens
28 housing
29 housing top aperture
30 housing front aperture
31 lower plate support
32 housing floor
34 viewing spot
35 optic cable receptor
36 fiber optic cable
38 film spool carrier
39 carrier housing
40 film axle crank
41 film spool axle
42 roller
44 film roll spool
50 photo detection apparatus
52 photomultiplier tube
54 monochrometer
56 control unit 58 oscilloscope
62 rotation arrow
64 arrow
66 arrow
68 butterfly bolt
70 lower plate support slot
80 computer interface
82 computer
84 analog to digital card
86 signal processing software

I claim:

1. A spot densitometer system comprising a viewing assembly comprising a flat spectrum lamp, a means for removing infrared light from the light emitted from said flat spectrum lamp, a means for supporting film, and a means for focusing light emitted by said flat spectrum lamp, whereby density of an entire width of a film emulsion being viewed through said viewing assembly is measured;

a photodetection apparatus comprising a means for converting light signals from said flat spectrum lamp into analog electrical signals;

a computer interface electrically connected to said means for converting light signals from said flat spectrum lamp into analog electrical signals;

wherein said means for supporting film comprises an upper plate rotatably attached to a lower plate, an upper plate aperture in said upper plate, a lower plate aperture in said lower plate, a housing comprising a housing top aperture and a viewing spot, said lower plate being attached to said housing; and a vertical height adjustment means for said film wherein said lower plate is attached to a plurality of lower plate supports, each said lower plate support comprising a lower plate support slot, each said lower plate support being attached to said housing by means of a bolt sized to freely fit through said lower plate support slot, whereby the vertical position of said lower plate is adjustable by loosening the bolt, repositioning said lower plate, and then re-tightening said bolt, thereby allowing the vertical position of said lower plate to be adjusted.

2. The spot densitometer system of claim 1 wherein said means for converting light signals from said flat spectrum lamp into analog electrical signals comprises a photomultiplier tube optically connected to said flat spectrum lamp, a monochromator electrically connected to said photomultiplier tube, and a control unit electrically attached to said photomultiplier tube and said monochromator.

3. The spot densitometer system of claim 1 wherein said means for focusing light emitted by said flat spectrum lamp comprises a focusing lens interposed between said flat spectrum lamp and said photodetection apparatus.

4. The spot densitometer system of claim 3 wherein said photodetection apparatus further comprises an oscilloscope electrically connected to said control unit.

5. The spot densitometer system of claim 3 wherein said photomultiplier tube is optically connected to said flat spectrum lamp by means of an optic cable receptor and a fiber optic cable.

6. The spot densitometer system of claim 1 wherein said means for removing infrared light from light emitted from said flat spectrum lamp comprises a condensing lens interposed between said flat spectrum lamp and said photodetection apparatus.

7. The spot densitometer system of claim 1 wherein said computer interface comprises an analog to digital card and signal processing software whereby analog electrical signals from said means for converting light signals from said flat spectrum lamp into analog electrical signals are reconverted into useful output formats comprising at least one of color density, relative exposure, and log relative exposure.

8. The spot densitometer system of claim 1 wherein said housing further comprises a housing floor having a viewing spot interposed between said means for focusing light emitted by said flat spectrum lamp and said photodetection apparatus.

9. The spot densitometer system of claim 1 further comprising at least two film spool carriers disposed on opposite sides of said lower plate, each said film spool carrier comprising a carrier housing, a film spool axle rotatably and slidably attached to said carrier housing, a film spool mounted on said film spool axle, a film axle crank rigidly attached to said film spool axle, and a roller rotatably attached to said carrier housing, whereby the position of film carried between said film spools is adjustable over said lower plate.

10. The spot densitometer system of claim 1 further comprising an exhaust fan and an exhaust chimney disposed close to said flat spectrum lamp whereby heat and ozone may be removed.

11. The spot densitometer system of claim 1 further comprising a power supply electrically connected to said flat spectrum lamp.

12. The spot densitometer of claim 1 wherein a shape of said viewing spot is circular.

* * * * *

UNITED STATES PATENT AND TRADEMARK OFFICE
CERTIFICATE OF CORRECTION

PATENT NO. : 5,617,213
DATED : April 1, 1997
INVENTOR(S) : Sun Fu-Shih

It is certified that error appears in the above-identified patent and that said Letters Patent is hereby corrected as shown below:

<u>Abstract line 6</u> "…focusing lens comprises a…" *should read* "…focusing lens, and viewing spot. The photodetection apparatus comprises a…"
<u>Column 1 line 23, 24</u> "…environment studies,…" *should read* "…environmental studies,…"
<u>Column 1 line 54</u> "In Addition" *should read* "In addition"
<u>Column 2 line 8, 9</u> "…increased case of use…" *should read* "…increased ease of use…"
<u>Column 4 line 14</u> "…(0.2% nms maximum)…" *should read* "…(0.2% rms maximum)…"
<u>Column 4 line 16,17</u> "…and possible burning…" *should read* "…and possibly burning…"
<u>Column 4 line 46</u> "…points. Point for calibration…" *should read* "…points. Points for calibration…"
<u>Column 5 line 59</u> "…taking the analog…" *should read* "…taking the antilog…"
<u>Column 6 line 10</u> "$RE_0 = RE / (\cos\theta)^a$" *should read* "$RE_0 = RE / (\cos\theta)^n$"
<u>Column 7 line 14</u> "A spot densitometer system comprising" *should read* "A spot densitometer system comprising:"

Signed and Sealed this

Twenty-fourth Day of June, 1997

*Attest:*

BRUCE LEHMAN

*Attesting Officer*   *Commissioner of Patents and Trademarks*